United States Patent [19]

Schmitt et al.

[11] Patent Number: 5,690,843
[45] Date of Patent: Nov. 25, 1997

[54] METHOD OF FABRICATING PRECISE CAST OR NONCAST IMPLANT-RETAINED DENTAL RESTORATIONS USING ELECTRICAL DISCHARGE MACHINING

[75] Inventors: Stephen M. Schmitt, San Antonio; David A. Chance, Helotes, both of Tex.

[73] Assignee: The United States of America as represented by the Secretary of the Air Force, Washington, D.C.

[21] Appl. No.: 581,795

[22] Filed: Jan. 2, 1996

[51] Int. Cl.$^6$ .............................. B23H 9/00; A61C 13/00; A61C 13/36
[52] U.S. Cl. .................... 219/69.17; 433/174; 433/223
[58] Field of Search .................... 219/69.17; 433/172, 433/173, 174, 223

[56] References Cited

U.S. PATENT DOCUMENTS

| | | | |
|---|---|---|---|
| 4,363,627 | 12/1982 | Windeler | 219/69.17 |
| 4,904,348 | 2/1990 | Domes et al. | 219/69.17 |
| 4,931,016 | 6/1990 | Sillard | 433/172 |
| 5,246,368 | 9/1993 | Sillard | 433/172 |

FOREIGN PATENT DOCUMENTS

| | | | |
|---|---|---|---|
| 4138803 | 5/1993 | Germany | 433/223 |

*Primary Examiner*—Geoffrey S. Evans
*Attorney, Agent, or Firm*—Bobby D. Scearce; Thomas L. Kundert

[57] ABSTRACT

A method of fabricating a precise implant-retained dental restoration from a casting or solid metal body by fabricating multiple electrodes, which are negatives of the surfaces of the desired restoration, and machining the casting or solid metal body against the electrodes by electrical discharge machining.

16 Claims, 7 Drawing Sheets

5,690,843

METHOD OF FABRICATING PRECISE CAST OR NONCAST IMPLANT-RETAINED DENTAL RESTORATIONS USING ELECTRICAL DISCHARGE MACHINING

FIELD OF THE INVENTION

This invention relates to a method of fabricating implant-retained dental restorations.

BACKGROUND OF THE INVENTION

Osseointegrated dental implants are placed in the patient's alveolar bone and the bone is allowed to heal in intimate contact with the implant surface. Unlike normal healthy teeth which are naturally mobile and can, to a certain extent, adapt themselves to the forces exerted upon them, dental implants are for all purposes "locked" in the bone. Implants do not possess the capability of adapting themselves to any deviation in the fit of implant-retained dental restorations. Delivering an implant restoration that does not tit precisely will overload the implants and may lead to such complications as loosening of retentive screws, fractures in the implants and possible loss of osseointegration. A single-tooth restoration must therefore fit precisely to the individual implant supporting it. For restorations supported by multiple implants, concern with fit is two-fold: first, the fit between the restoration and each individual implant in the patient's mouth must be precise; and second, the intraoral fit of the entire restoration to the multiple implants must be precise.

Implant-retained dental restorations are commonly fabricated by two methods, both of which incorporate the conventional "lost wax" technique. The first method employs custom plastic patterns which are designed to allow the restoration to begin directly at the implant so that it may emerge from the patient's gums with a natural appearance. This method is described in a published article which appeared in The International Journal of Oral and Maxillofacial Implants, Vol. 3, Number 3, 1988 at pages 183–189 "The 'UCLA' Abutment", Lewis, S. G. et al. In this method, a master cast is made from an impression of the patient's mouth. The master cast contains implant replicas in the proper position. Plastic patterns, which are designed to fit precisely to the implant replicas, are secured to the master cast. A wax pattern of the restoration is developed on the plastic patterns, which thus become part of the framework design. Ultimately, the wax and plastic patterns are invested, burnt out, and a casting is made in accordance with the "lost wax" technique. The cast restoration should fit directly to the implants, just as the plastic patterns fit to the implant replicas. Unfortunately, errors are often created due the many variables involved in the casting process. These variables include distortion of the wax pattern, improper mixing of the investment, distortion in the setting of the investment, improper burnout of the investment, improper melting of the alloy and improper cooling of the metal after casting. This results in a restoration that may not fit precisely to each individual implant in the patient's mouth. To correct such errors, it is necessary to either recast the restoration or refine the metal surface with a milling or lapping tool.

It is recommended to use alloys containing a high content of a noble metal, such as gold, to help reduce, although not eliminate, such casting errors. Unfortunately, the advantages of using these alloys are counterbalanced by the disadvantage of very high cost.

For multiple-implant restorations, an additional fit-related concern exists. Even if the fit between the restoration and each individual implant can be corrected, the casting will still not fit intraorally if the relationship of the implants to each other is not correct on the master cast. Unfortunately, despite careful attention to detail in its fabrication, the master cast often has slight discrepancies in relation to the implant replicas. Clinically, even minor discrepancies in the fit of the restoration to the implants can cause failure. To correct such errors in intraoral fit, the restoration is cut, or cast, in individual pieces, one for each implant. The individual pieces are later soldered together in the correct position in the dental laboratory.

A second common method for fabricating implant-retained dental restorations employs premachined components, which allow the restoration to begin as close as 1 mm from the top of the implant. These components generally include abutments, which are machined to fit precisely to the tops of the implants; gold-alloy cylinders, which are machined to fit precisely over the abutments; and gold screws, which retain the gold cylinders to the abutments. This method is described in The International Journal of Oral and Maxillofacial Implants, Volume 6, Number 2, 1991 at pages 195–201 "An Esthetic Titanium Abutment: Report of a Technique", Lewis, S. G.

In this method, the gold cylinders are placed on one or more abutment replicas in the master cast and a wax pattern is developed which incorporates the gold cylinders. After investing, the wax burns out and the gold cylinders become part of the cast framework, thereby eliminating many of the variables that compromise the results of the plastic pattern-burnout method. The casting is delivered by placing the gold cylinders over the abutments in the patient's mouth. Unfortunately, the advantages of using these precisely-fitting components are counterbalanced by their cost.

Moreover, despite the close tolerances between the premachined components, there is still concern with the intraoral fit of the entire restoration to multiple implants. As indicated previously, despite care in its fabrication, the master cast often has slight discrepancies in relation to the abutment replicas. To correct errors in intraoral fit, the restoration is cut, or cast, in individual pieces which are soldered together in the laboratory. This is a difficult, time-consuming process and often creates an inferior metal substructure.

The need therefore exists for a simple, cost-effective method of fabricating implant-retained dental restorations that fit perfectly and passively to the implants in the patient's mouth. Applicants' method is directed towards the solution of this problem by providing for precise fitting of cast restorations supported by single or multiple implants by electrical discharge machining (EDM).

EDM is a process that uses electrical discharges to machine electrically conductive materials. During the machining process, the work piece is eroded by controlled electrical discharge from an electrode. The discharge from the electrode removes metal from the work piece at the shortest gap distance. Each spark removes a small amount of metal and the process can be repeated by as many as 250,000 times a second. This process is accomplished with an EDM apparatus that maintains the electrode-to-work piece relationship, a power source that produces the electrical energy, and a dielectric liquid, similar to light oil, in which the electrode and work piece are immersed. The EDM apparatus has a hydraulic ram, which moves the electrode close to the work piece, and a work tank, in which the dielectric liquid is held.

Applicants' method may be used to machine castings fabricated with plastic patterns or with premachined components by EDM. This method may also be used to machine castings which are fabricated from wax patterns created by applying wax directly to the implant replicas. In addition, this invention provides for the machining of the occlusal surface of an implant-retained cast restoration by EDM.

Applicants' invention allows for the use of inexpensive metals, in lieu of gold alloys, in the casting process. Titanium is very biocompatable and much less expensive than gold alloys. However, precision casting of titanium is very difficult. This invention corrects problems associated with roughness and fit of castings fabricated from inexpensive metals.

EDM is used to improve the fit of cast crowns and bridges in U.S. Pat. No. 4,363,627 and U.S. Pat. No. 5,246,368. EDM is also used to improve the fit between a cast substructure, securable to abutments in the patient's mouth, and a female supra structure incorporating the restoration in U.S. Pat. No. 4,931,016. However, EDM has not heretofore been used to machine implant-retained cast restorations to ensure precise fit to implants.

Applicants' invention also allows for the fabrication of a precise single-tooth or multiple-implant restoration from a solid body of metal, dispensing with the "lost wax" technique altogether. EDM is used in this invention to machine the tissue, implant and occlusal surfaces of a restoration from a solid body, or ingot, of metal. Any metal that can be machined with EDM can be used in this method. Titanium is ideal because of its excellent biocompatability and low cost. EDM is used to fabricate crowns and bridges from a solid matrix body in U.S. Pat. No. 5,227,602. However, EDM has not heretofore been used to fabricate precisely fitting implant-retained restorations from a solid body of metal.

OBJECTS OF THE INVENTION

It is an object of the present invention to fabricate a precise implant-retained restoration from a casting created by the "lost wax" technique by machining the implant or abutment and occlusal surfaces of the casting by electrical discharge machining. It is a further object of the invention to fabricate a precise implant-retained restoration from a solid body, or ingot, of metal by machining the tissue, implant and occlusal surfaces of the ingot by electrical discharge machining.

SUMMARY OF THE INVENTION

The invention describes a method of fabricating precise cast and noncast implant-retained dental restorations. The method comprises the fabrication of multiple electrodes which are "negative" replicas of the surfaces of the desired restoration. After the electrodes are fabricated, the restoration is machined against the appropriate electrodes with electric discharge machining (EDM).

For a cast restoration, two electrodes are fabricated: first, an electrode which is a negative replica of the implant or abutment surface of fie restoration, that is, the surface of the restoration which will fit to the implants or abutments in the patient's mouth; and second, an electrode which is a negative replica of the occlusal surface of the restoration. The first electrode is referred to as the "electrode block" and the second electrode is referred to as the "occlusal electrode". For a noncast restoration, an additional electrode must be fabricated: an electrode which is a negative replica of the tissue surface of the restoration, that is, the surface of the restoration which will rest against the tissues in the patient's mouth. This third electrode is referred to as the "tissue electrode".

DETAILED DESCRIPTION OF THE INVENTION

Figure 1:
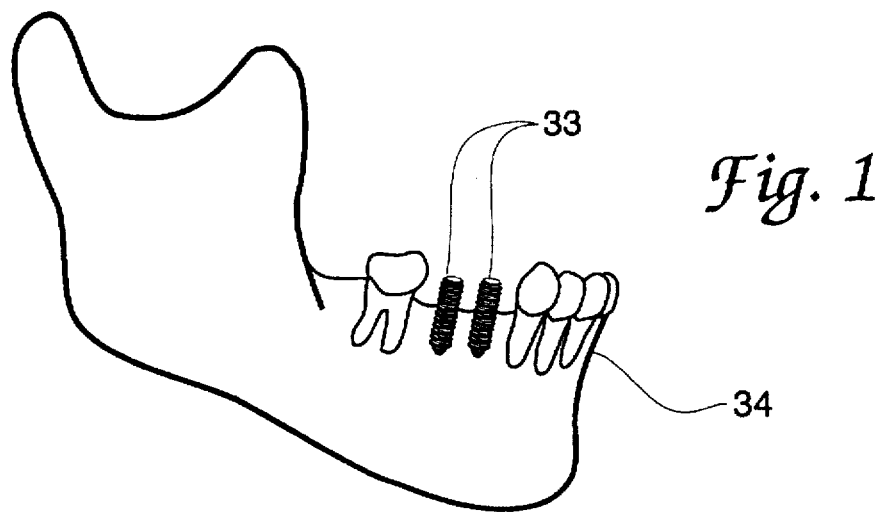
FIG. 1 shows dental implants mounted in a patient's alveolar bone.
Figure 2:
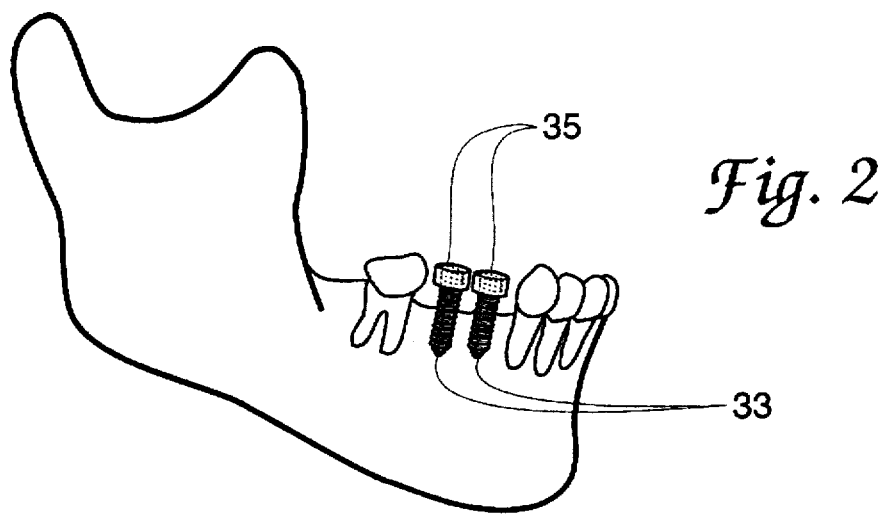
FIG. 2 shows abutments secured to implants mounted in the patient's alveolar bone.
Figure 3:
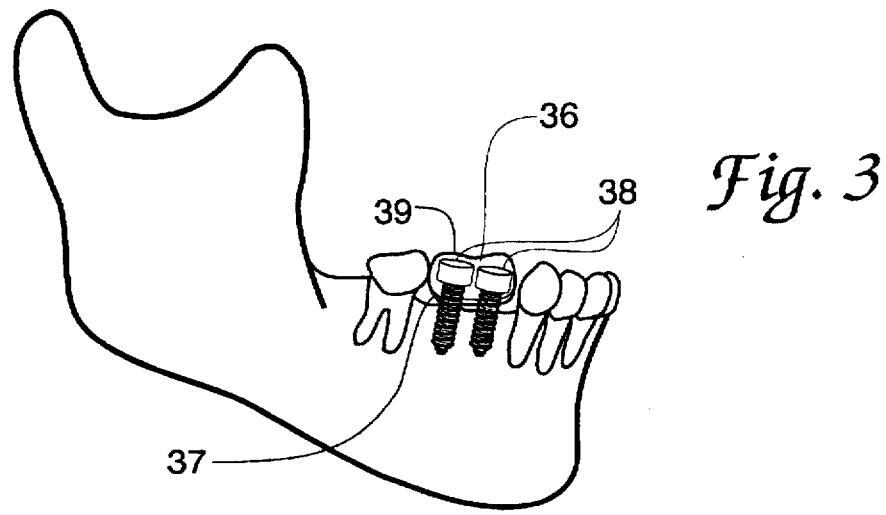
FIG. 3 shows a desired metallic dental restoration which has an ideal occlusal surface and which fits precisely to implants mounted in the patient's alveolar bone.

For purposes of illustration only, it will be presumed that a multiple-implant restoration is to be fabricated. Any deviations that are required for fabrication of a single-tooth restoration will be explained. As shown in FIG. 1, it will be presumed that two implants 33 are mounted at predetermined locations in the patient's alveolar bone 34. As shown in FIG. 2, abutments 35 are mounted to the implants 33 in those instances where the restoration is to be fabricated with premachined components. As shown in FIG. 3, the dental restoration 36 fabricated by Applicants' inventive process has an ideal occlusal surface and fits precisely to the implants or abutments. The restoration's tissue surface 37, implant or abutment surface 38 and occlusal surface 39 are machined to attain such anatomical correctness and precise fit.

Figure 4:
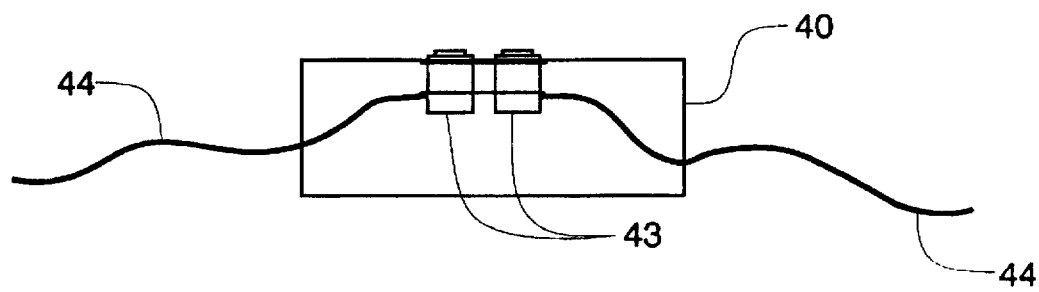
FIG. 4 shows an electrode block which is a negative replica of the surface of the implants or abutments in the patient's mouth.
Figure 5:
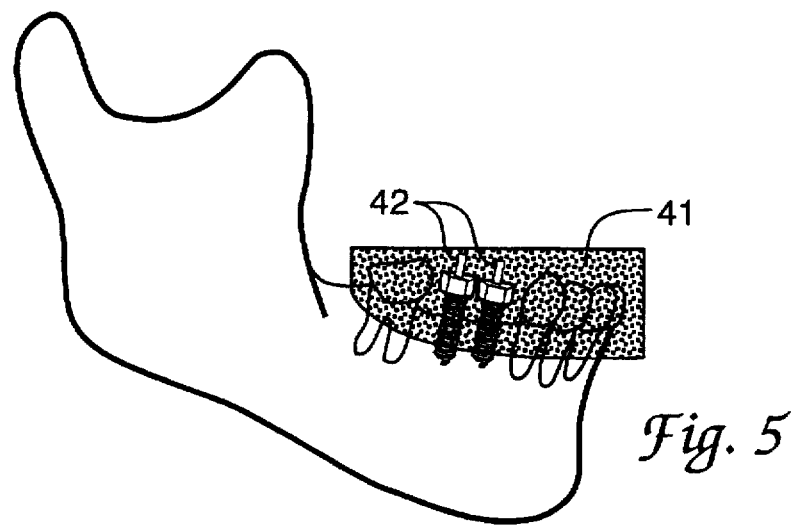
FIG. 5 shows an impression taken of implants or abutments in the patient's mouth.
Figure 6:
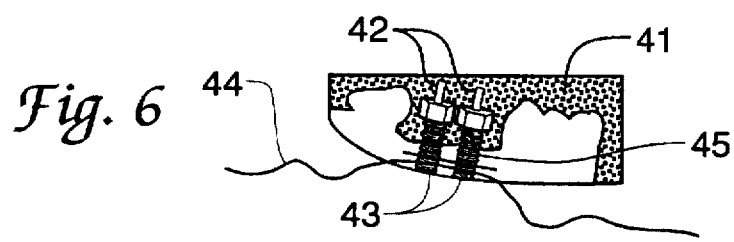
FIG. 6 shows implant or abutment replicas attached to impression copings in the impression.

The first step in Applicants' inventive process is the fabrication of the electrode block 40 illustrated in FIG. 4. Referring now to FIG. 5, an impression 41 is first made of the implants 33 or abutments 35 in the patient's mouth with impression copings 42. This procedure is well known in the dental art. Next, as shown in FIG. 6, a brass, copper or graphite replica 43 is attached to each coping 42 in the impression 41. Brass, copper or graphite implant replicas are used for noncast restorations and cast restorations fabricated with wax or wax and plastic patterns. For restorations fabricated with wax and premachined components, brass, copper or graphite abutment replicas are used. Copper wire 44 is next attached to each replica 43 to provide electrical contact. The replicas 43 are luted together with a strong luting agent and a plurality of pieces of rigid wire 45 so that when the replicas 43 are removed from the impression 41, they will remain in the same relative positions as the corresponding copings 42 in the impression 41.

Figure 7:
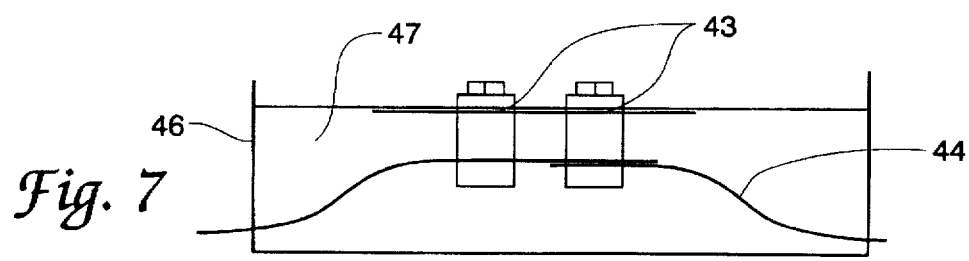
FIG. 7 shows the method for forming the electrode block from a wax enclosure surrounding the implant or abutment replicas which is poured in dental stone.

As shown in FIG. 7, the replicas 43 are removed from the impression and "boxed", that is, a sheet of soft wax is molded to form the sides of a wax enclosure or "box" 46 surrounding the replicas 43. The copper wires 44 attached to the replicas 43 are allowed to protrude through openings in the sides of the box 46. Next, low expansion dental stone 47 is poured into the box 46 to a level such that the replicas 43 protrude above the surface of the dental stone 47 but are rigidly held in their relative positions when the dental stone 47 hardens. After the dental stone 47 is set, the wax enclosure 46 is removed.

As shown in FIG. 4, the dental stone 47 hardens to form an electrode block 40 having a base, sides, from which protrude copper wires 44, and a top from which protrude replicas 43 which are rigidly held in stone in the same relative positions as the implants 33 in the patient's mouth.

For a single-tooth restoration, a similar procedure is followed. Copper wire is attached to a replica (brass, copper or graphite implant replicas for noncast restorations and cast restorations fabricated with wax or wax and plastic patterns; brass, copper or graphite abutment replicas for restorations fabricated with wax and premachined components). The replica is "boxed" and poured with dental stone which hardens to form an electrode block.

The electrode block 40 is thus a negative replica of the implant or abutment surface 38 of the restoration 36 illustrated in FIG 3. The electrode block 40 will be used in an electrical discharge machining (EDM) process to correct any errors in the fit of the restoration 36 to the implants 33 or abutments 35 in the patient's mouth. Usually, at least two such electrode blocks 40 will be needed to properly machine the restoration.

Figure 8:
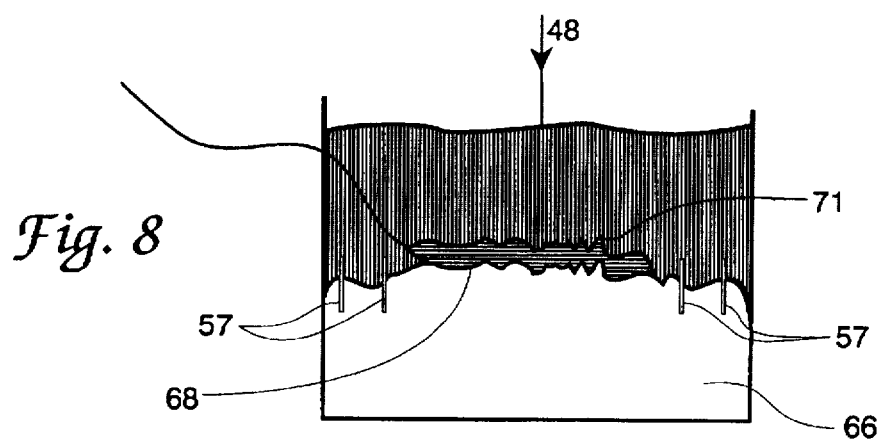
FIG. 8 shows a copper plated occlusal electrode which is a negative replica of the occlusal surface of the desired restoration.
Figure 9:
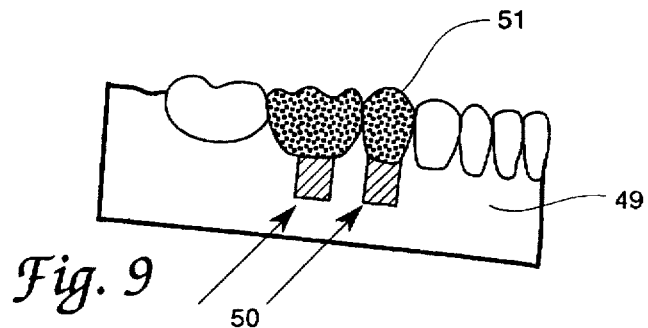
FIG. 9 shows a master cast of the patient's dental arch.

The next step in Applicants' inventive process is the fabrication of the occlusal electrode 48 illustrated in FIG 8. To make the occlusal electrode 48, a master cast 49, shown in FIG. 9 is created by a well-known process. In this process, a brass, copper or graphite replica 50 is attached to each coping 42 in the impression 41. Implant replicas are used for noncast restorations and cast restorations made with wax or wax and plastic patterns. Abutment replicas are used for cast restorations made with wax and premachined components. The impression 41 is poured in dental stone which hardens to form the master cast 49, which is a positive replica of the patient's dental arch. The next step is to form a pattern 51 of the restoration on the master cast 49 by the desired method. The pattern 51 formed should have the ideal contour and occlusion of the desired restoration 36 illustrated in FIG. 3.

Figure 10:
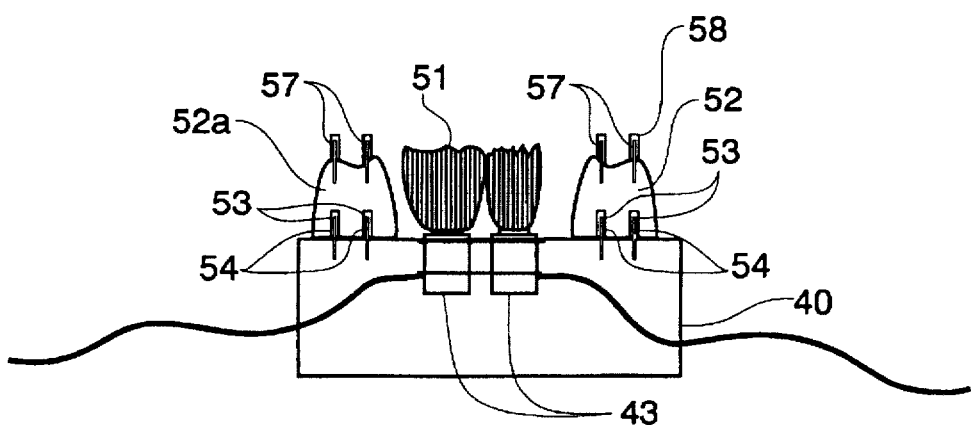
FIG. 10 shows a pattern of the desired restoration positioned between two stone walls and on top of the electrode block.
Figure 11:
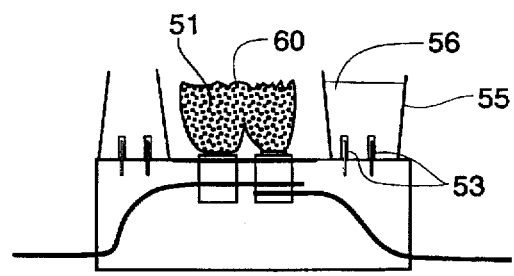
FIG. 11 shows the method for forming the two stone walls which are indexed to the electrode block.

As shown in FIG. 10, the pattern 51 is removed from the master cast 49 and positioned on the electrode block 40. Next, two "stone walls" 52, 52a are fabricated on the electrode block 40 on opposing sides of the pattern 51. The stone walls 52, 52a will be used to precisely position the occlusal electrode relative to the restoration during the EDM process. To fabricate the first wall 52, a plurality of holes sized to receive indexing pins 53 are drilled into a section of the top of the electrode block 40 adjacent to the pattern 51. Indexing pins 53 are inserted in the holes such that they extend axially from the top of the electrode block 40. Indexing pin sleeves 54 are added to the pins. As illustrated in FIG. 11, the pins 53 are "boxed" with a sheet of soft wax 55 and a low expansion dental stone 56 is poured into the box 55 to a level approximately equal to the occlusal surface 60 of the adjacent pattern 51. As shown in FIG. 10, the stone hardens to form a stone wall 52 which is removably positioned upon, and indexed to, the electrode block 40 by indexing pins 53. In a similar manner, a stone wall 52a of approximately equal size is formed on the opposing side of the pattern 51. Next, a plurality of holes sized to receive indexing pins 57 are drilled in the tops of each of the stone walls 52, 52a. Indexing pins 57 are inserted in the holes such that they extend axially from the tops of the stone walls 52, 52a. Indexing pin sleeves 58 are added to the pins 57.

Figure 13:
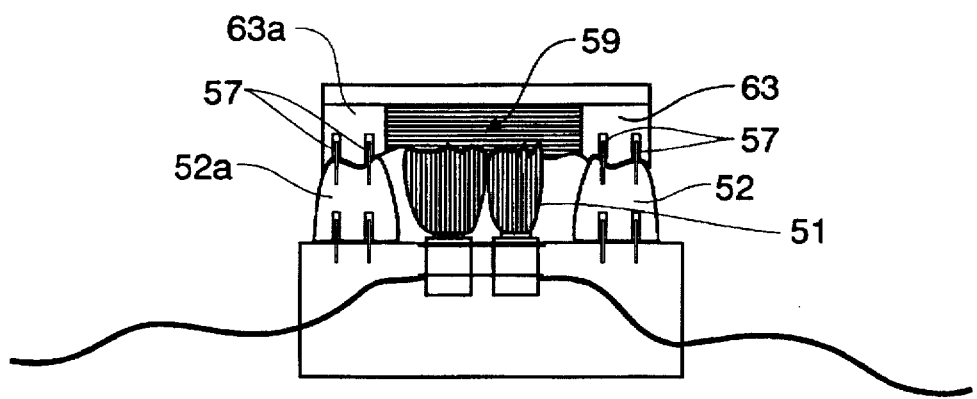
FIG. 13 shows an impression of the occlusal surface of the pattern positioned between the two stone members and on top of the plastic pattern and adjacent stone walls.
Figure 12:
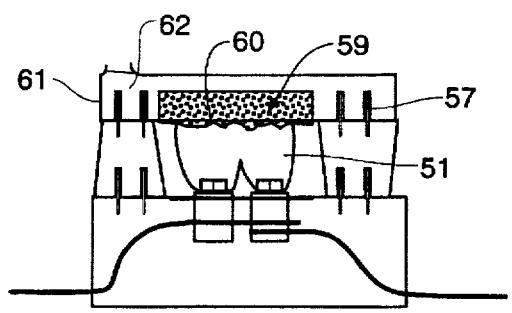
FIG. 12 shows the method for forming two stone members which are indexed to the stone walls.

As shown in FIG. 12, an impression 59 is made of the occlusal surface 60 of the pattern 51 in a suitable moldable material, such as addition reaction silicone or polysulfide rubber. The impression 59 and adjacent indexing pins 57 are next "boxed" with a sheet of soft wax 61 and poured with a low expansion dental stone 62. As shown in FIG. 13, the stone hardens to form stone members 63, 63a which are indexed to the stone walls 52, 52a by indexing pins 57.

Figure 14:
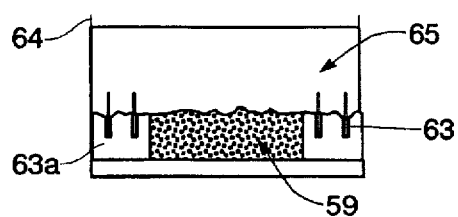
FIG. 14 shows the method for forming a positive stone replica of the occlusal surface of the pattern.
Figure 15:
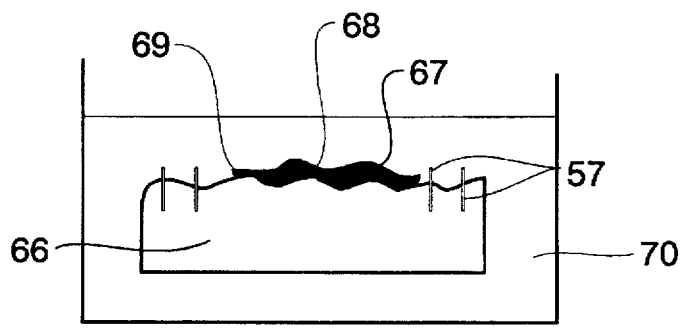
FIG. 15 shows the method for galvanically plating the positive stone replica of the occlusal surface of the pattern with copper.

As shown in FIG. 14, the impression 59 and adjacent stone members 63, 63a are removed from the pattern and "boxed" with a sheet of soft wax 64 which is poured with low expansion dental stone 65. As illustrated in FIG. 15, the stone hardens to form a cast 66 which is indexed to the stone members 63, 63a by indexing pins 57. The cast 66 is a positive stone replica of the occlusal surface 60 of the pattern 51.

Figure 16:
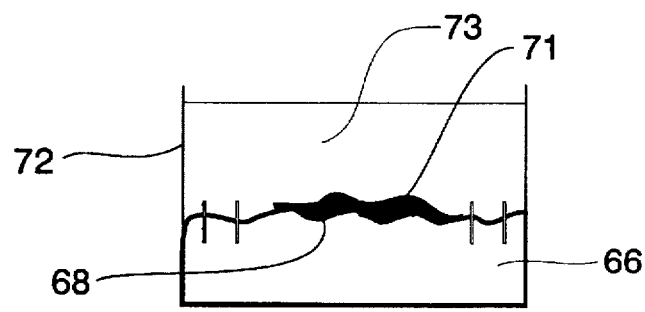
FIG. 16 shows the method for forming the occlusal electrode.

The occlusal surface 67 of the cast 66 is made conductive by coating it with a very thin film of graphite 68. The graphite film is so thin that its thickness maybe disregarded. Copper wire 69 is attached to the graphite-plated surface 68 of the cast 66 to create electrical contact. The cast 66 is then submerged in an acid copper plating bath 70. As shown in FIG. 16, copper plating 71 is allowed to galvanically plate on the graphite surface 68 to a thickness on the order of 0.5–1 mm.

The cast 66 is "boxed" with a sheet of soft wax 72 and a low expansion dental stone 73 is poured against the copper plating 71. As shown in FIG. 8, after the stone 73 hardens, the cast 66 is removed with mechanical and air abrasion, leaving a copper-plated electrode 48 which is a negative replica of the occlusal surface 60 of the pattern 51. The occlusal electrode 48 is indexed to the stone walls 52, 52a by indexing pins 57. This occlusal electrode 48 will be used in the EDM process to machine the occlusal surface 39 of the restoration 36 illustrated in FIG. 3.

Figure 17:
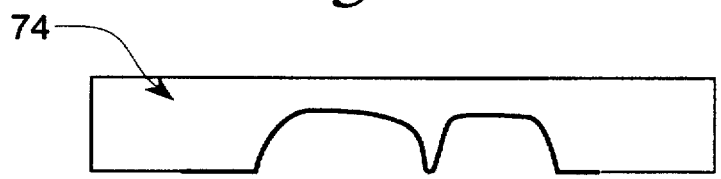
FIG. 17 shows a galvanically plated copper tissue electrode which is a negative replica of the tissue surface of the pattern.
Figure 18:
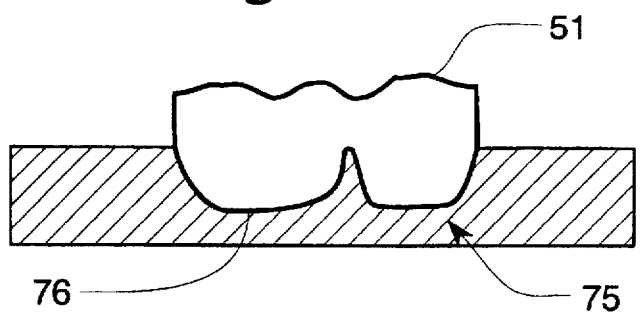
FIG. 18 shows an impression taken of the tissue surface of the pattern.

If the restoration is to be fabricated from a solid metal body, or ingot, it is also necessary to fabricate a tissue electrode 74, illustrated in FIG. 17. First, as shown in FIG. 18, an impression 75 is made of the tissue surface 76 of the pattern 51. The tissue electrode 74 is fabricated from the impression 75 in a process substantially the same as that illustrated in FIGS. 14 to 16. The impression 75 is "boxed" with a sheet of soft wax and poured in dental stone, which hardens to form a cast. The cast is a positive stone replica of the tissue surface 76 of the pattern 51. The tissue surface of the cast is made conductive by coating it with a very thin film of graphite. The graphite film is so thin that its thickness may be disregarded. Copper wire is attached to the graphite-plated surface of the cast to create electrical contact. The cast is then submerged in an acid copper plating bath. The copper plating is allowed to galvanically plate on the graphite surface to a thickness on the order of 0.5–1 mm. The cast is "boxed" with a sheet of soft wax and a low expansion dental stone is poured against the copper plating. After the stone hardens, the cast is removed with mechanical and air abrasion, leaving a copper-plated tissue electrode 74 which is a negative replica of the tissue surface 76 of the pattern 51. The tissue electrode 74 will be used in the EDM process to machine the tissue surface of the restoration.

If a cast restoration is desired, the pattern is cast in an appropriate metal using the "lost wax" technique.

The restoration, cast or noncast, is next machined against the appropriate electrodes by EDM. If the restoration is noncast, that is, fabricated from a metal ingot, then the ingot's tissue surface, implant surface and occlusal surface must be machined in the order indicated. If the restoration is cast, the implant or abutment surface of the casting is first machined and, if desired, the occlusal surface is then machined. The machining of these surfaces in the EDM apparatus is now described.

Figure 19:
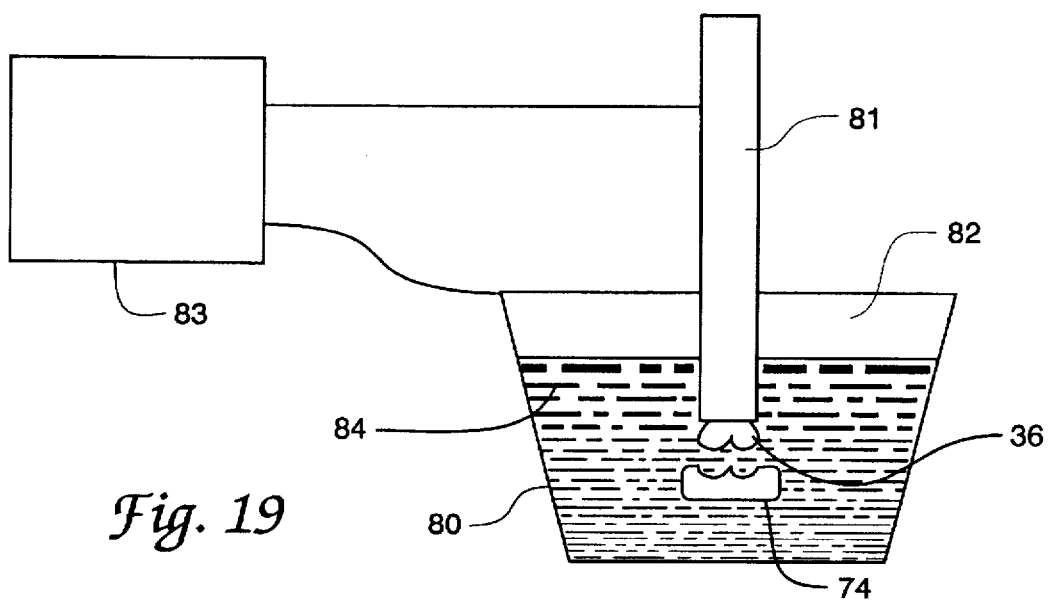
FIG. 19 shows a metallic implant-retained restoration positioned in an electric discharge machining apparatus in proper position for final machining.
Figure 20:
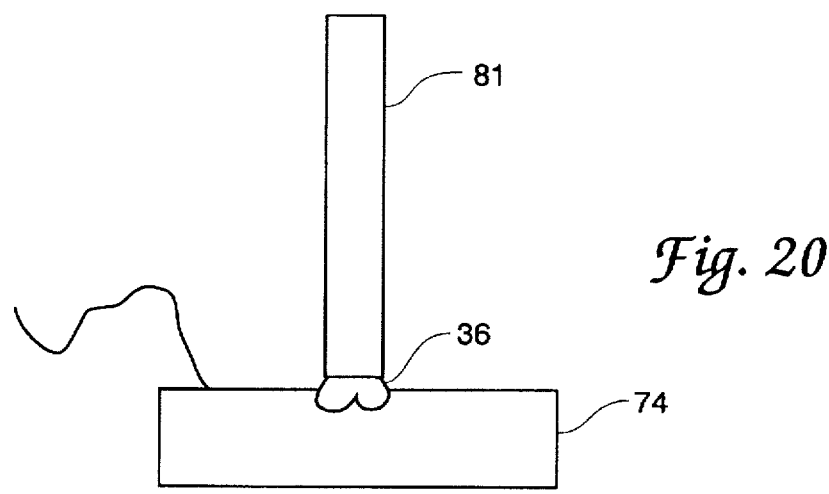
FIG. 20 shows final machining of the metallic implant-retained restoration against the tissue electrode.

FIG. 19 schematically depicts the principal elements of the EDM apparatus 80. The apparatus has a hydraulic ram 81 and a work tank 82 which are mounted on a common frame (not shown). The EDM power source 83 produces electrical energy. To machine the tissue surface 37, the noncast dental restoration 36, is connected to the ram 81 of the EDM apparatus 80. The tissue electrode 74 is releasably supported in a suitable holding fixture (not shown for clarity) at the bottom of the work tank 82. The ram 81 and tissue electrode 74 must be positioned to be in approximate axial alignment. A suitable liquid dielectric 84 is added to the tank 82 after the noncast restoration 36 and the tissue electrode 74 are aligned. Specific reference is now made to FIG. 20 which shows the final machining process (the work tank, dielectric and power source are not shown for clarity). The ram 81 is lowered, bringing the noncast restoration 36 and tissue electrode 74 into very close proximity with each other such that erosion occurs with respect to the noncast restoration 36 such that it conforms exactly to the configuration of the tissue electrode 74. The noncast restoration 36 is machined to have about 0.002 mm tolerance between the tissue electrode 74 and the corresponding tissue surface 37 of the noncast restoration 36.

Figure 21:
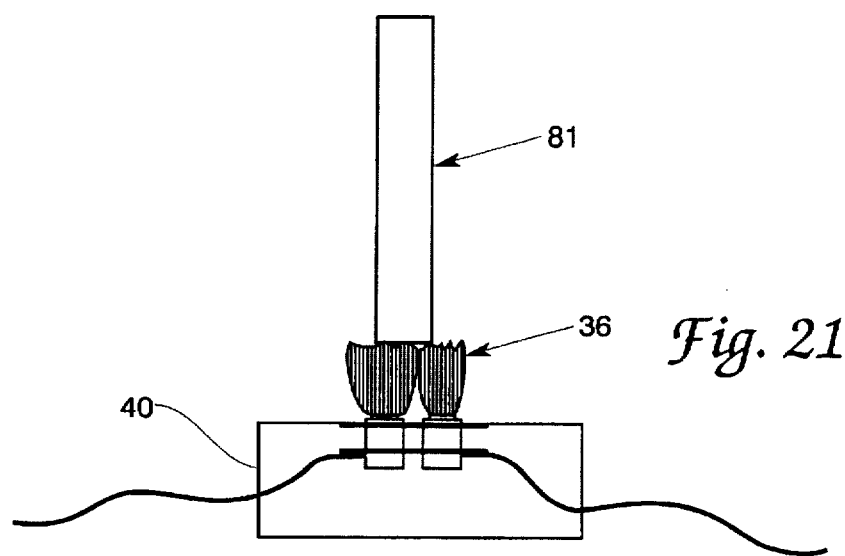
FIG. 21 shows final machining of the metallic implant-retained restoration against the electrode block.

To machine the implant or abutment surface 38, the occlusal surface 39 of the restoration 36, cast or noncast, is connected to the ram 81. The electrode block 40 is releasably supported in the work tank 82. The restoration 36 and electrode block 40 must be positioned to be in axial and radial alignment. The dielectric 84 is added to the tank 82 after the restoration 36 and the electrode block 40 are aligned. As shown in FIG. 21, the ram 81 is lowered, bringing the restoration 36 and electrode block 40 into very close proximity with each other such that erosion occurs with respect to the restoration 36 such that it fits intimately to the electrode block 40. The restoration 36 is machined to have about 0.002 mm tolerance between the electrode block 40 and the corresponding implant or abutment surface 38 of the restoration 36. Usually, two electrode blocks 40 are needed to properly machine the implant or abutment surface 38 of the restoration 36.

Figure 22:
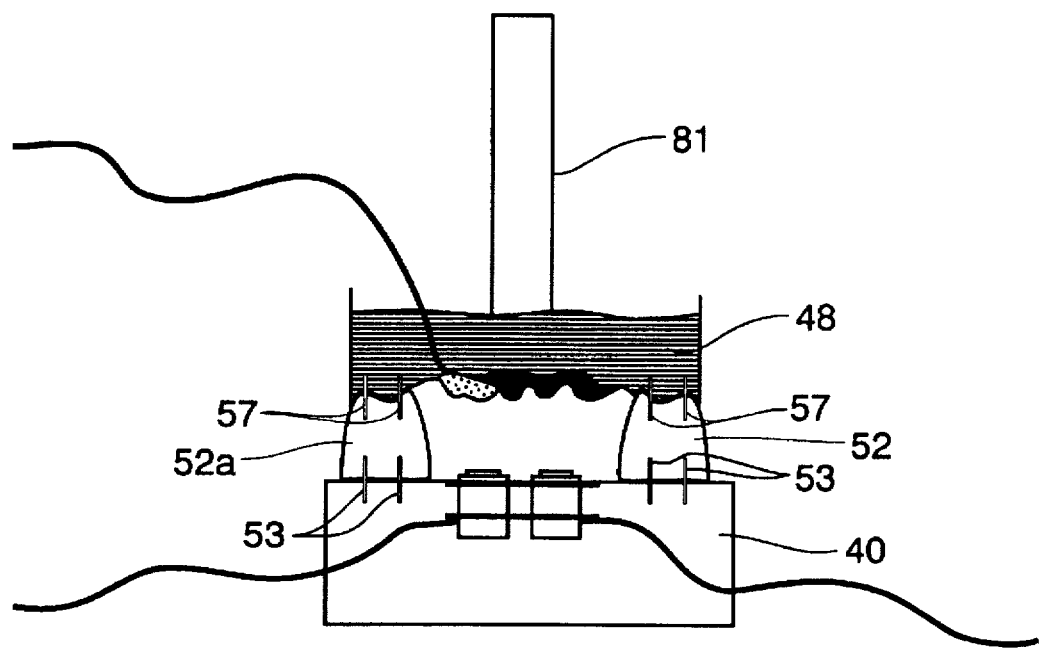
FIG. 22 shows the method for positioning the occlusal electrode on the ram of the electric discharge machining apparatus.

To machine the occlusal surface 39 of the restoration 36, the occlusal electrode 48 is connected to the ram 81. The electrode block 40 is releasably supported in the work tank 82. The occlusal electrode 48 and restoration 36 must be positioned to be in axial and radial alignment. As shown in FIG. 22, to obtain this precise positioning, the stone walls 52, 52a are first positioned on, and indexed to, the electrode block 40 by indexing pins 53. The occlusal electrode 48 is positioned on, and indexed to, the stone walls 52, 52a by indexing pins 57. The ram 81 is lowered and brought down over the occlusal electrode 48. The occlusal electrode 88 is connected to the ram 81 and the vertical position of the ram 81 is noted. The ram 81 and occlusal electrode 48 are raised and moved away from the electrode block 40. The stone walls 52, 52a are removed from the electrode block 40.

Figure 23:
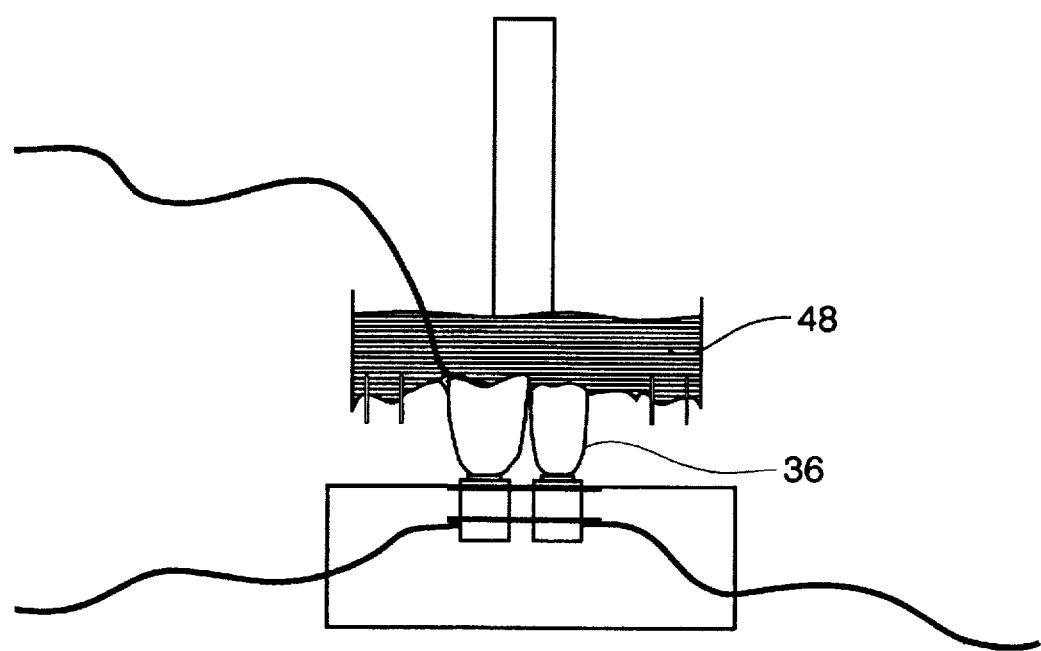
FIG. 23 shows final machining of the metallic implant-retained restoration against the occlusal electrode.

Next, the restoration 36 is positioned to fit securely to the electrode block 40. The dielectric 84 is added to the tank 82 and the ram 81 is lowered to the prior noted position, bringing the restoration 36 and occlusal electrode 48 into very close proximity with each other. As shown in FIG. 23, the occlusal surface 39 of the restoration 36 is eroded to conform exactly to the configuration of the occlusal electrode 48. The restoration 36 is machined to have about 0.002 mm tolerance between the occlusal electrode 48 and the corresponding occlusal surface 39 of the restoration.

The teachings of all patents, journal articles and other references cited herein are incorporated herein by reference.

The invention therefore provides a novel method for fabricating a precise implant-retained dental restoration from a solid metal casting machined by EDM. It is understood that modifications to the invention may be made as might occur to one with skill in the field of the invention within the scope of the appended claims. All embodiments contemplated thereunder which achieve the objects of the invention have therefore not been shown in complete detail. Other embodiments may be developed without departing from the spirit of the invention or from the scope of the appended claims.

We claim:

1. A method of fabricating an anatomically correct dental restoration for installation on an implant mounted at a predetermined location in the alveolar bone of a patient, said restoration having a cavity coinciding with said implant for securely mounting said restoration to said implant, said method comprising the following steps:

(a) fabricating a rough cast restoration from a pattern having the desired configuration of said restoration;

(b) fabricating a first accurate electrode conforming to the configuration of said implant; and, (c) in an electric discharge machine, mounting said rough cast restoration in radial and axial alignnment with said first electrode, with said first electrode in alignment with the corresponding cavity of said rough restoration and finish machining said cavity of said rough restoration to the configuration of said first electrode by electric discharge machining.

2. A method of fabricating an anatomically correct dental restoration for installation on a plurality of implants mounted at predetermined locations in the alveolar bone of a patient, said restoration having a plurality of cavities coinciding with said implants for securely mounting said restoration to said implants, said method comprising the following steps:

(a) fabricating a rough cast restoration from a pattern having the desired configuration of said restoration;

(b) fabricating a first accurate electrode conforming to the configuration of said implants; and, (c) in an electric discharge machine, mounting said rough cast restoration and said first electrode in axial and radial alignment with said first electrode in alignment with the corresponding cavities of said rough restoration, and finish machining said cavities of said rough restoration to the configuration of said first electrode by electric discharge machining.

3. A method of fabricating an anatomically correct dental restoration for installation on a plurality of metallic abutments secured to a plurality of implants mounted at predetermined locations in the alveolar bone of a patient, each said abutment secured to a corresponding implant, said restoration having cavities coinciding with said abutments for securely mounting said restoration to said abutments, said method comprising the following steps:

(a) fabricating a rough cast restoration from a pattern having the desired configuration of said restoration, said rough restoration comprising solidified molten metal cast to a plurality of prefabricated metallic components, each said component having a cavity coinciding with a corresponding abutment for securely mounting said components to said abutments;

(b) fabricating a first accurate electrode conforming to the configuration of said abutments; and, (c) in an electric discharge machine, mounting said rough cast restoration in radial and axial alignment with said first electrode, with said first electrode in alignment with said cavities of said rough restoration, and finish machining said cavities of said rough restoration to the configuration of said first electrode by electric discharge machining.

4. A method of fabricating an anatomically correct dental restoration configured to be worn in contact with a finite area of tissue in the mouth of a patient and securely mounted to an implant placed at a predetermined location in the alveolar bone of said patient, said method comprising the following steps:

(a) fabricating a first accurate electrode conforming to the configuration of said implant, (b) fabricating a second accurate metallic electrode configured to a negative replica of the desired occlusal area of said restoration;

(c) fabricating a third accurate metallic electrode configured to said finite area of tissue;

(d) employing the electrodes in an electric discharge machining process to form the dental restoration from a solid matrix body.

5. A method of fabricating an anatomically correct dental restoration configured to be worn in contact with a finite area of tissue in the mouth of a patient and mounted to a plurality of implants placed at predetermined locations in the alveolar bone of said patient, said method comprising the following steps:

(a) fabricating a first accurate electrode conforming to the configuration of said implants;

(b) fabricating a second accurate metallic electrode configured to a negative replica of the desired occlusal area of said restoration;

(c) fabricating a third accurate metallic electrode configured to said finite area of tissue; and, (d) employing the electrodes in an electric discharge machining process to form the dental restoration from a solid matrix body.

6. A method as in claims 1, 2 or 3 including the further steps of:

fabricating a second accurate metallic electrode configured to a negative replica of the desired occlusal area of said restoration and, in an electric discharge machine, mounting said rough cast restoration and said second electrode in radial and axial alignment with said second electrode in alignment with the corresponding occlusal area of said rough restoration, and finish machining said occlusal area of said rough restoration to the configuration of said second electrode by electric discharge machining.

7. A method as in claims 1 or 4 wherein the first accurate electrode is fabricated by:

attaching a copper wire having a first end and a second end to an implant replica conforming to the configuration of said implant, molding a sheet of wax to form the sides and base of a wax enclosure surrounding said implant replica such that the second end of the copper wire extends from said sides, and pouring dental stone into said wax enclosure such that said dental stone hardens to form an accurate electrode.

8. A method as in claims 2 or 5 wherein the first accurate electrode is fabricated by taking an impression in the mouth of said patient of said implants, said impression containing a plurality of impression copings at locations in said impression corresponding to the locations of said implants in the alveolar bone of said patient, attaching an implant replica to each said impression coping, each said implant replica conforming to the configuration of each corresponding implant, attaching a copper wire having a first end and a second end to each said implant replica at said first end, securing said implant replicas together such that the implant replicas are rigidly held in their locations relative to one another, removing said replicas from said impression, molding a sheet of wax to form the sides and base of a wax enclosure surrounding said implant replicas such that the second ends of the copper wires extend from said sides, pouring dental stone into said wax enclosure such that said dental stone hardens to form an accurate electrode containing implant replicas at locations in said hardened dental stone corresponding to the locations of said implants in the alveolar bone of said patient.

9. A method according to claim 3 wherein the first accurate electrode is fabricated by taking an impression in the mouth of said patient of said implants, said impression containing a plurality of impression copings at locations in said impression corresponding to the locations of said implants in the alveolar bone of said patient, attaching an abutment replica to each said impression coping, each said abutment replica conforming to the configuration of each corresponding abutment, attaching a copper wire having a first end and a second end to each said abutment replica at said first end, securing said abutment replicas together such that the abutment replicas are rigidly held in their locations relative to one another, removing said abutment replicas from said impression, molding a sheet of wax to form the sides and base of a wax enclosure surrounding said abutment replicas such that the second ends of the copper wires extend from said sides, pouring dental stone into said wax enclosure such that said dental stone hardens to form an accurate electrode containing abutment replicas at locations in said hardened dental stone corresponding to the locations of said implants in the alveolar bone of said patient.

10. A method according to claim 6 wherein the second metallic electrode is fabricated by taking an impression of the occlusal area of said pattern, forming a dental cast of said impression, coating the occlusal area of said dental cast with an electrically conductive material, galvanically plating over said electrically conductive material a layer of copper, molding a sheet of wax around the sides of said dental cast to form a wax enclosure, pouting dental stone into said wax enclosure and over said copper-plated occlusal area and, after said dental stone hardens, removing said dental cast.

11. A method according to claim 6 wherein said second electrode is fabricated by:

taking an impression of the desired occlusal area of said pattern, positioning said pattern on said first electrode, fabricating first and second orienting members on opposing sides of said pattern such that said first and second members are removably positioned on said first electrode, positioning said occlusal impression on said pattern and between said first and second members, fabricating third and fourth orienting members on opposing sides of said occlusal impression such that said third and fourth members are removably positioned on said first and second members, removing said occlusal impression and said third and fourth members from said pattern, forming a dental cast of said occlusal impression and said third and fourth members such that said dental cast is removably positioned on said third and fourth members, coating the occlusal area of said dental cast with an electrically conductive material, galvanically plating over said electrically conductive material a layer of copper, molding a sheet of wax around the sides of said dental cast to form a wax enclosure, pouring dental stone into said wax enclosure and over said copper-plated occlusal area and, after said dental stone hardens, removing said dental cast.

12. A method according to claim 11 wherein said second electrode is placed in axial and radial alignment with said rough cast restoration by:

positioning said first and second orienting members on said first electrode, positioning said second electrode on said first and second members, lowering the ram of said electric discharge machine to said second electrode, connecting said second electrode to said ram, raising said ram and second electrode away from said first electrode, removing said first and second members from said first electrode, and mounting said rough cast restoration to said first electrode.

13. A method as in claims 4 or 5 wherein the second metallic electrode is fabricated by taking an impression of the occlusal area of said pattern, forming a dental cast of said impression, coating the occlusal area of said dental cast with an electrically conductive material, galvanically plating over said electrically conductive material a layer of copper, molding a sheet of wax around the sides of said dental cast to form a wax enclosure, pouting dental stone into said wax enclosure and over said copper-plated occlusal area and, after said dental stone hardens, removing said dental cast.

14. A method as in claim 4 or 5 wherein the third metallic electrode is fabricated by preparing a master cast of the patient's mouth, said master cast including said finite area of tissue, preparing a pattern on said master cast to the desired configuration of said restoration, removing said pattern from the master cast, taking an impression of the tissue area of said pattern, forming a dental cast of said impression, coating the tissue area of said dental cast with an electrically conductive material, galvanically plating over said electrically conductive material a layer of copper, molding a sheet of wax around the sides of said dental cast to form a wax enclosure, pouring dental stone into said wax enclosure and over said copper-plated tissue area and, after said dental stone hardens, removing said dental cast.

15. A method as in claims 4 or 5 wherein said second electrode is fabricated by:

preparing a master cast of the patient's mouth, preparing a pattern on said master cast to the desired configuration of said restoration, taking an impression of the desired occlusal area of said pattern, positioning said pattern on said second electrode, fabricating first and second orienting members on opposing sides of said pattern, positioning said occlusal impression on said pattern and between said first and second members, fabricating third and fourth orienting members on opposing sides of said occlusal impression such that said third and fourth members are removably positioned on said first and second members, removing said occlusal impression and said third and fourth members from said occlusal impression, forming a dental cast of said occlusal impression and said third and fourth members such that said dental cast is removably positioned on said third and fourth members, coating the occlusal area of said dental cast with an electrically conductive material, galvanically plating over said electrically conductive material a layer of copper, molding a sheet of wax around the sides of said dental cast to form a wax enclosure, pouring dental stone into said wax enclosure and over said copper-plated occlusal area and, after said dental stone hardens, removing said dental cast.

16. A method defined in claim 15 wherein said electrodes are employed in an electric discharge machining process to form the dental restoration from a solid matrix body having a top area and a bottom area by sequentially in an electric discharge machine, mounting said solid matrix body and said third electrode in axial and radial alignment with said third electrode in alignment with the bottom area of said solid body and finish machining said bottom area to the configuration of said third electrode by electric discharge machining, in said electric discharge machine, mounting said solid matrix body and said first electrode in axial and radial alignment with said first electrode in alignment with the bottom area of said solid body and finish machining said bottom area to the configuration of said first electrode by electric discharge machining, and in said electric discharge machine, mounting said solid matrix body and said second electrode in radial and axial alignment electrode with said second electrode in alignment with the top area of said solid body by positioning said first and second orienting members on said first electrode, positioning said second electrode on said first and second members, lowering the ram of said electric discharge machine to said second electrode, connecting said second electrode to said ram, raising said ram and second electrode away from said first electrode, removing said first and second members from said first electrode, mounting said solid body on said second electrode, and finish machining said top area to the configuration of said second electrode by electric discharge machining.

* * * * *